US008888792B2

(12) United States Patent
Harris et al.

(10) Patent No.: US 8,888,792 B2
(45) Date of Patent: Nov. 18, 2014

(54) TISSUE APPOSITION CLIP APPLICATION DEVICES AND METHODS

(75) Inventors: Jason L. Harris, Mason, OH (US); James T. Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1543 days.

(21) Appl. No.: 12/172,766

(22) Filed: Jul. 14, 2008

(65) Prior Publication Data

US 2010/0010511 A1  Jan. 14, 2010

(51) Int. Cl.
A61B 17/10   (2006.01)
A61B 17/08   (2006.01)
A61B 17/29   (2006.01)
A61B 17/00   (2006.01)

(52) U.S. Cl.
CPC .............. *A61B 17/10* (2013.01); *A61B 17/29* (2013.01); *A61B 17/083* (2013.01); *A61B 2017/00818* (2013.01)
USPC ............................ 606/142; 606/143; 606/139

(58) Field of Classification Search
CPC .............. A61B 17/064; A61B 17/068; A61B 17/0682; A61B 17/072; A61B 17/07207; A61B 17/1222; A61B 17/128; A61B 17/1285; A61B 17/122; A61B 17/1227; A61B 2017/0053; A61B 2017/0488; A61B 2017/0688; A61B 2017/07271
USPC ........................................ 606/139, 142, 143
See application file for complete search history.

(56) References Cited

U.S. PATENT DOCUMENTS

| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |

(Continued)

FOREIGN PATENT DOCUMENTS

| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Dianne Dornbusch

(57) ABSTRACT

Surgical instruments and methods for closing a gastrotomy. In various embodiments, the surgical instrument may comprise an overtube that supports a clip magazine therein that houses a plurality of tissue apposition clips in an orientation wherein the upper and lower clip arms thereof are releasably supported in an open orientation. Various embodiments are configured to operably accommodate one or more tissue grasping members for grasping the tissue. Other embodiments comprise clip dispensing adapters that may be affixed to the distal end of an endoscope. The various adapters are configured to support a tissue apposition clip such that the upper and lower clip arms thereof are initially supported in an open orientation relative to each other to enable grasped tissue to be drawn therein. Various tissue apposition clips are disclosed which may be used in connection with conventional tissue anchors and/or sutures.

14 Claims, 13 Drawing Sheets

(56) References Cited

U.S. PATENT DOCUMENTS

| | | | |
|---|---|---|---|
| 2,113,246 A | | 4/1938 | Wappler |
| 2,155,365 A | | 4/1939 | Rankin |
| 2,191,858 A | | 2/1940 | Moore |
| 2,196,620 A | | 4/1940 | Attarian |
| 2,388,137 A | | 10/1945 | Graumlich |
| 2,493,108 A | | 1/1950 | Casey, Jr. |
| 2,504,152 A | | 4/1950 | Riker et al. |
| 2,938,382 A | | 5/1960 | De Graaf |
| 2,952,206 A | | 9/1960 | Becksted |
| 3,069,195 A | | 12/1962 | Buck |
| 3,170,471 A | | 2/1965 | Schnitzer |
| 3,435,824 A | | 4/1969 | Gamponia |
| 3,470,876 A | | 10/1969 | Barchilon |
| 3,595,239 A | | 7/1971 | Petersen |
| 3,669,487 A | | 6/1972 | Roberts et al. |
| 3,746,881 A | | 7/1973 | Fitch et al. |
| 3,799,672 A | | 3/1974 | Vurek |
| 3,854,473 A | | 12/1974 | Matsuo |
| 3,946,740 A | | 3/1976 | Bassett |
| 3,948,251 A | | 4/1976 | Hosono |
| 3,994,301 A | | 11/1976 | Agris |
| 4,011,872 A | | 3/1977 | Komiya |
| 4,012,812 A | | 3/1977 | Black |
| 4,085,743 A | | 4/1978 | Yoon |
| 4,164,225 A | | 8/1979 | Johnson et al. |
| 4,178,920 A | | 12/1979 | Cawood, Jr. et al. |
| 4,207,873 A | | 6/1980 | Kruy |
| 4,235,238 A | | 11/1980 | Ogiu et al. |
| 4,258,716 A | | 3/1981 | Sutherland |
| 4,269,174 A | | 5/1981 | Adair |
| 4,278,077 A | | 7/1981 | Mizumoto |
| 4,285,344 A | | 8/1981 | Marshall |
| 4,311,143 A | | 1/1982 | Komiya |
| 4,329,980 A | | 5/1982 | Terada |
| 4,396,021 A | | 8/1983 | Baumgartner |
| 4,406,656 A | | 9/1983 | Hattler et al. |
| 4,452,246 A | | 6/1984 | Bader et al. |
| 4,461,281 A | | 7/1984 | Carson |
| 4,491,132 A | | 1/1985 | Aikins |
| 4,492,232 A | * | 1/1985 | Green .......... 606/143 |
| 4,527,331 A | | 7/1985 | Lasner et al. |
| 4,527,564 A | | 7/1985 | Eguchi et al. |
| 4,538,594 A | | 9/1985 | Boebel et al. |
| D281,104 S | | 10/1985 | Davison |
| 4,569,347 A | | 2/1986 | Frisbie |
| 4,580,551 A | | 4/1986 | Siegmund et al. |
| 4,646,722 A | | 3/1987 | Silverstein et al. |
| 4,653,476 A | | 3/1987 | Bonnet |
| 4,655,219 A | | 4/1987 | Petruzzi |
| 4,669,470 A | | 6/1987 | Brandfield |
| 4,671,477 A | | 6/1987 | Cullen |
| 4,685,447 A | | 8/1987 | Iversen et al. |
| 4,711,240 A | | 12/1987 | Goldwasser et al. |
| 4,712,545 A | | 12/1987 | Honkanen |
| 4,721,116 A | | 1/1988 | Schintgen et al. |
| 4,733,662 A | | 3/1988 | DeSatnick et al. |
| D295,894 S | | 5/1988 | Sharkany et al. |
| 4,763,669 A | | 8/1988 | Jaeger |
| 4,770,188 A | | 9/1988 | Chikama |
| 4,791,707 A | * | 12/1988 | Tucker .......... 227/19 |
| 4,796,627 A | * | 1/1989 | Tucker .......... 606/143 |
| 4,815,450 A | | 3/1989 | Patel |
| 4,823,794 A | | 4/1989 | Pierce |
| 4,829,999 A | | 5/1989 | Auth |
| 4,867,140 A | | 9/1989 | Hovis et al. |
| 4,873,979 A | | 10/1989 | Hanna |
| 4,880,015 A | | 11/1989 | Nierman |
| 4,911,148 A | | 3/1990 | Sosnowski et al. |
| 4,926,860 A | | 5/1990 | Stice et al. |
| 4,934,364 A | * | 6/1990 | Green .......... 606/143 |
| 4,938,214 A | | 7/1990 | Specht et al. |
| 4,950,273 A | | 8/1990 | Briggs |
| 4,950,285 A | | 8/1990 | Wilk |
| 4,960,133 A | | 10/1990 | Hewson |
| 4,977,887 A | | 12/1990 | Gouda |
| 4,979,950 A | | 12/1990 | Transue et al. |
| 4,984,581 A | | 1/1991 | Stice |
| 4,990,152 A | * | 2/1991 | Yoon .......... 606/140 |
| 5,007,917 A | | 4/1991 | Evans |
| 5,010,876 A | | 4/1991 | Henley et al. |
| 5,020,514 A | | 6/1991 | Heckele |
| 5,020,535 A | | 6/1991 | Parker et al. |
| 5,025,778 A | | 6/1991 | Silverstein et al. |
| 5,026,379 A | * | 6/1991 | Yoon .......... 606/141 |
| 5,033,169 A | | 7/1991 | Bindon |
| 5,037,433 A | | 8/1991 | Wilk et al. |
| 5,041,129 A | | 8/1991 | Hayhurst et al. |
| 5,046,513 A | | 9/1991 | Gatturna et al. |
| 5,050,585 A | | 9/1991 | Takahashi |
| 5,052,372 A | | 10/1991 | Shapiro |
| 5,065,516 A | | 11/1991 | Dulebohn |
| 5,066,295 A | | 11/1991 | Kozak et al. |
| 5,123,913 A | | 6/1992 | Wilk et al. |
| 5,123,914 A | | 6/1992 | Cope |
| 5,133,727 A | | 7/1992 | Bales et al. |
| 5,147,374 A | | 9/1992 | Fernandez |
| 5,174,300 A | | 12/1992 | Bales et al. |
| 5,176,126 A | | 1/1993 | Chikama |
| 5,190,050 A | | 3/1993 | Nitzsche |
| 5,190,555 A | | 3/1993 | Wetter et al. |
| 5,192,284 A | | 3/1993 | Pleatman |
| 5,201,752 A | | 4/1993 | Brown et al. |
| 5,201,908 A | | 4/1993 | Jones |
| 5,203,785 A | | 4/1993 | Slater |
| 5,203,787 A | | 4/1993 | Noblitt et al. |
| 5,209,747 A | | 5/1993 | Knoepfler |
| 5,217,003 A | | 6/1993 | Wilk |
| 5,217,453 A | | 6/1993 | Wilk |
| 5,219,357 A | | 6/1993 | Honkanen et al. |
| 5,219,358 A | | 6/1993 | Bendel et al. |
| 5,222,362 A | | 6/1993 | Maus et al. |
| 5,222,965 A | | 6/1993 | Haughton |
| 5,234,437 A | | 8/1993 | Sepetka |
| 5,234,453 A | | 8/1993 | Smith et al. |
| 5,235,964 A | | 8/1993 | Abenaim |
| 5,242,456 A | * | 9/1993 | Nash et al. .......... 606/142 |
| 5,246,424 A | | 9/1993 | Wilk |
| 5,259,366 A | | 11/1993 | Reydel et al. |
| 5,263,958 A | | 11/1993 | deGuillebon et al. |
| 5,273,524 A | | 12/1993 | Fox et al. |
| 5,275,607 A | | 1/1994 | Lo et al. |
| 5,284,128 A | | 2/1994 | Hart |
| 5,284,162 A | | 2/1994 | Wilk |
| 5,287,845 A | | 2/1994 | Faul et al. |
| 5,290,299 A | * | 3/1994 | Fain et al. .......... 606/142 |
| 5,290,302 A | | 3/1994 | Pericic |
| 5,295,977 A | | 3/1994 | Cohen et al. |
| 5,297,536 A | | 3/1994 | Wilk |
| 5,301,061 A | | 4/1994 | Nakada et al. |
| 5,312,333 A | | 5/1994 | Churinetz et al. |
| 5,312,351 A | | 5/1994 | Gerrone |
| 5,312,416 A | | 5/1994 | Spaeth et al. |
| 5,312,423 A | | 5/1994 | Rosenbluth et al. |
| 5,320,636 A | | 6/1994 | Slater |
| 5,325,845 A | | 7/1994 | Adair |
| 5,330,471 A | | 7/1994 | Eggers |
| 5,330,486 A | | 7/1994 | Wilk |
| 5,330,488 A | | 7/1994 | Goldrath |
| 5,330,496 A | | 7/1994 | Alferness |
| 5,330,502 A | | 7/1994 | Hassler et al. |
| 5,331,971 A | | 7/1994 | Bales et al. |
| 5,334,198 A | | 8/1994 | Hart et al. |
| 5,344,428 A | | 9/1994 | Griffiths |
| 5,350,391 A | | 9/1994 | Iacovelli |
| 5,352,184 A | | 10/1994 | Goldberg et al. |
| 5,352,222 A | | 10/1994 | Rydell |
| 5,354,302 A | | 10/1994 | Ko |
| 5,354,311 A | | 10/1994 | Kambin et al. |
| 5,356,408 A | | 10/1994 | Rydell |
| 5,364,408 A | | 11/1994 | Gordon |
| 5,364,410 A | | 11/1994 | Failla et al. |
| 5,366,466 A | | 11/1994 | Christian et al. |
| 5,366,467 A | | 11/1994 | Lynch et al. |
| 5,368,605 A | | 11/1994 | Miller, Jr. |

(56) References Cited

U.S. PATENT DOCUMENTS

| | | |
|---|---|---|
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A * | 2/1997 | Stefanchik et al. ........... 606/143 |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A * | 12/1997 | Yoon ........................... 606/157 |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,725,542 A * | 3/1998 | Yoon ........................... 606/157 |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,720 A * | 7/1998 | Walder-Utz et al. ........... 606/151 |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |

(56) References Cited

U.S. PATENT DOCUMENTS

| | | | |
|---|---|---|---|
| 5,817,119 A | 10/1998 | Klieman et al. | |
| 5,819,736 A | 10/1998 | Avny et al. | |
| 5,824,071 A | 10/1998 | Nelson et al. | |
| 5,827,281 A | 10/1998 | Levin | |
| 5,827,299 A | 10/1998 | Thomason et al. | |
| 5,830,221 A * | 11/1998 | Stein et al. | 606/157 |
| 5,830,231 A | 11/1998 | Geiges, Jr. | |
| 5,833,700 A | 11/1998 | Fogelberg et al. | |
| 5,833,703 A | 11/1998 | Manushakian | |
| 5,843,017 A | 12/1998 | Yoon | |
| 5,843,121 A * | 12/1998 | Yoon | 606/206 |
| 5,849,022 A | 12/1998 | Sakashita et al. | |
| 5,853,374 A | 12/1998 | Hart et al. | |
| 5,855,585 A | 1/1999 | Kontos | |
| 5,860,913 A | 1/1999 | Yamaya et al. | |
| 5,860,995 A | 1/1999 | Berkelaar | |
| 5,868,762 A | 2/1999 | Cragg et al. | |
| 5,876,411 A | 3/1999 | Kontos | |
| 5,882,331 A | 3/1999 | Sasaki | |
| 5,882,344 A | 3/1999 | Stouder, Jr. | |
| 5,893,846 A | 4/1999 | Bales et al. | |
| 5,893,874 A | 4/1999 | Bourque et al. | |
| 5,893,875 A | 4/1999 | O'Connor et al. | |
| 5,899,919 A | 5/1999 | Eubanks, Jr. et al. | |
| 5,902,254 A | 5/1999 | Magram | |
| 5,904,702 A | 5/1999 | Ek et al. | |
| 5,906,625 A * | 5/1999 | Bito et al. | 606/142 |
| 5,908,420 A | 6/1999 | Parins et al. | |
| 5,911,737 A | 6/1999 | Lee et al. | |
| 5,916,147 A | 6/1999 | Boury | |
| 5,921,993 A | 7/1999 | Yoon | |
| 5,921,997 A | 7/1999 | Fogelberg et al. | |
| 5,922,008 A | 7/1999 | Gimpelson | |
| 5,925,052 A | 7/1999 | Simmons | |
| 5,928,255 A | 7/1999 | Meade et al. | |
| 5,928,266 A | 7/1999 | Kontos | |
| 5,936,536 A | 8/1999 | Morris | |
| 5,944,718 A | 8/1999 | Austin et al. | |
| 5,951,549 A | 9/1999 | Richardson et al. | |
| 5,954,720 A | 9/1999 | Wilson et al. | |
| 5,954,731 A | 9/1999 | Yoon | |
| 5,957,943 A | 9/1999 | Vaitekunas | |
| 5,957,953 A | 9/1999 | DiPoto et al. | |
| 5,971,995 A | 10/1999 | Rousseau | |
| 5,976,074 A | 11/1999 | Moriyama | |
| 5,976,075 A | 11/1999 | Beane et al. | |
| 5,976,130 A | 11/1999 | McBrayer et al. | |
| 5,976,131 A | 11/1999 | Guglielmi et al. | |
| 5,980,539 A | 11/1999 | Kontos | |
| 5,980,556 A | 11/1999 | Giordano et al. | |
| 5,984,938 A | 11/1999 | Yoon | |
| 5,984,939 A | 11/1999 | Yoon | |
| 5,989,182 A | 11/1999 | Hori et al. | |
| 5,993,447 A | 11/1999 | Blewett et al. | |
| 5,997,555 A | 12/1999 | Kontos | |
| 6,001,120 A | 12/1999 | Levin | |
| 6,004,269 A | 12/1999 | Crowley et al. | |
| 6,004,330 A | 12/1999 | Middleman et al. | |
| 6,007,566 A | 12/1999 | Wenstrom, Jr. | |
| 6,010,515 A | 1/2000 | Swain et al. | |
| 6,012,494 A | 1/2000 | Balazs | |
| 6,019,770 A | 2/2000 | Christoudias | |
| 6,024,708 A | 2/2000 | Bales et al. | |
| 6,024,747 A | 2/2000 | Kontos | |
| 6,027,522 A | 2/2000 | Palmer | |
| 6,030,365 A | 2/2000 | Laufer | |
| 6,030,634 A | 2/2000 | Wu et al. | |
| 6,033,399 A | 3/2000 | Gines | |
| 6,036,685 A | 3/2000 | Mueller | |
| 6,053,927 A | 4/2000 | Hamas | |
| 6,066,160 A | 5/2000 | Colvin et al. | |
| 6,068,603 A | 5/2000 | Suzuki | |
| 6,068,629 A | 5/2000 | Haissaguerre et al. | |
| 6,071,233 A | 6/2000 | Ishikawa et al. | |
| 6,074,408 A | 6/2000 | Freeman | |
| 6,086,530 A | 7/2000 | Mack | |
| 6,090,108 A | 7/2000 | McBrayer et al. | |
| 6,096,046 A | 8/2000 | Weiss | |
| 6,102,926 A | 8/2000 | Tartaglia et al. | |
| 6,106,473 A | 8/2000 | Violante et al. | |
| 6,109,852 A | 8/2000 | Shahinpoor et al. | |
| 6,110,154 A | 8/2000 | Shimomura et al. | |
| 6,110,183 A | 8/2000 | Cope | |
| 6,113,593 A | 9/2000 | Tu et al. | |
| 6,117,144 A | 9/2000 | Nobles et al. | |
| 6,117,158 A | 9/2000 | Measamer et al. | |
| 6,139,555 A | 10/2000 | Hart et al. | |
| 6,146,391 A | 11/2000 | Cigaina | |
| 6,148,222 A | 11/2000 | Ramsey, III | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1 | 5/2001 | Marchand | |
| 6,234,958 B1 | 5/2001 | Snoke et al. | |
| 6,245,079 B1 | 6/2001 | Nobles et al. | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,541 B1 * | 3/2002 | Kienzle et al. | 606/143 |
| 6,352,543 B1 | 3/2002 | Cole | |
| 6,355,035 B1 | 3/2002 | Manushakian | |
| 6,361,534 B1 | 3/2002 | Chen et al. | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,391,029 B1 | 5/2002 | Hooven et al. | |
| 6,402,735 B1 | 6/2002 | Langevin | |
| 6,406,440 B1 | 6/2002 | Stefanchik | |
| 6,409,733 B1 | 6/2002 | Conlon et al. | |
| 6,427,089 B1 | 7/2002 | Knowlton | |
| 6,431,500 B1 | 8/2002 | Jacobs et al. | |
| 6,443,970 B1 | 9/2002 | Schulze et al. | |
| 6,443,988 B2 | 9/2002 | Felt et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,458,076 B1 | 10/2002 | Pruitt | |
| 6,464,701 B1 | 10/2002 | Hooven et al. | |
| 6,464,702 B2 | 10/2002 | Schulze et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,627 B1 | 12/2002 | Komi | |

(56) References Cited

U.S. PATENT DOCUMENTS

| | | |
|---|---|---|
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,520,954 B2 | 2/2003 | Ouchi |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,545 B2 * | 11/2003 | Shipp et al. ............... 606/157 |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 * | 6/2004 | Smith et al. ............... 606/142 |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,767,356 B2 * | 7/2004 | Kanner et al. ............... 606/213 |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 * | 11/2005 | Sixto et al. ............... 606/153 |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,011,669 B2 * | 3/2006 | Kimblad ............... 606/151 |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,056,330 B2 * | 6/2006 | Gayton ............... 606/219 |
| 7,060,024 B2 | 6/2006 | Long et al. |
| 7,060,025 B2 | 6/2006 | Long et al. |
| 7,063,697 B2 | 6/2006 | Slater |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |

(56) References Cited

U.S. PATENT DOCUMENTS

| | | |
|---|---|---|
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,207,997 B2* | 4/2007 | Shipp et al. .................. 606/157 |
| 7,208,005 B2 | 4/2007 | Frecker et al. |
| 7,211,092 B2* | 5/2007 | Hughett ........................ 606/142 |
| 7,220,227 B2 | 5/2007 | Sasaki et al. |
| 7,223,271 B2* | 5/2007 | Muramatsu et al. ........... 606/143 |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,674,259 B2 | 3/2010 | Shadduck |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,758,577 B2 | 7/2010 | Nobis et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,815,662 B2 | 10/2010 | Spivey et al. |
| 7,828,186 B2 | 11/2010 | Wales |
| 7,833,238 B2* | 11/2010 | Nakao ............................ 606/151 |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,075,587 B2 | 12/2011 | Ginn |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1* | 6/2002 | Sixto et al. .................... 606/142 |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |

(56) References Cited

U.S. PATENT DOCUMENTS

| | | |
|---|---|---|
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0138682 A1* | 7/2004 | Onuki et al. ............... 606/144 |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1* | 11/2004 | Michlitsch et al. .......... 600/106 |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0090842 A1* | 4/2005 | Suzuki et al. ............... 606/148 |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1* | 9/2005 | Nakao .......................... 606/142 |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251158 A1* | 11/2005 | Saadat et al. ................. 606/153 |
| 2005/0251166 A1 | 11/2005 | Vaughan et al. |
| 2005/0251176 A1* | 11/2005 | Swanstrom et al. .......... 606/153 |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |

(56) References Cited

U.S. PATENT DOCUMENTS

| | | |
|---|---|---|
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0154460 A1 | 7/2007 | Kraft et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |

(56) References Cited

U.S. PATENT DOCUMENTS

| | | |
|---|---|---|
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0306493 A1* | 12/2008 | Shibata et al. ............ 606/143 |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0023032 A1 | 1/2010 | Granja Filho |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152888 A1* | 6/2011 | Ho et al. ............... 606/143 |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0774918 B1 | 4/2004 |
| EP | 0931515 B1 | 8/2004 |
| EP | 0941128 B1 | 10/2004 |
| EP | 1411843 B1 | 10/2004 |

(56) References Cited

FOREIGN PATENT DOCUMENTS

| | | |
|---|---|---|
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

(56) References Cited

OTHER PUBLICATIONS

K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
"Z-Offset Technique Used in the Introduction of Trocar During Laparoscopic Surgery," M.S. Hershey NOTES Presentation to EES NOTES Development Team, Sep. 27, 2007.
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
U.S. Appl. No. 11/437,440, filed May 19, 2006.
U.S. Appl. No. 11/274,352, filed Nov. 15, 2005.
U.S. Appl. No. 11/744,271, filed May 4, 2007.
U.S. Appl. No. 11/744,279, filed May 4, 2007.
U.S. Appl. No. 11/437,864, filed May 19, 2006.
U.S. Appl. No. 11/274,358, filed Nov. 15, 2005.
U.S. Appl. No. 11/274,354, filed Nov. 15, 2005.
U.S. Appl. No. 11/706,685, filed Feb. 15, 2007.
U.S. Appl. No. 11/706,460, filed Feb. 15, 2007.
U.S. Appl. No. 11/706,591, filed Feb. 15, 2007.
U.S. Appl. No. 11/706,766, filed Feb. 15, 2007.
U.S. Appl. No. 11/706,811, filed Feb. 15, 2007.
U.S. Appl. No. 11/715,710, filed Mar. 8, 2007.
U.S. Appl. No. 11/796,357, filed Apr. 27, 2007.
U.S. Appl. No. 11/894,358, filed Aug. 21, 2007.
U.S. Appl. No. 11/986,084, filed Nov. 20, 2007.
U.S. Appl. No. 12/014,417, filed Jan. 5, 2008.
U.S. Appl. No. 11/981,070, filed Oct. 31, 2007.
U.S. Appl. No. 11/968,810, filed Jan. 3, 2008.
U.S. Appl. No. 11/981,078, filed Oct. 31, 2007.
U.S. Appl. No. 11/998,370, filed Nov. 29, 2007.
U.S. Appl. No. 11/986,420, filed Nov. 21, 2007.
U.S. Appl. No. 12/019,461, filed Jan. 24, 2008.
U.S. Appl. No. 11/897,676, filed Aug. 31, 2007.
U.S. Appl. No. 12/109,673, filed Apr. 25, 2008.
U.S. Appl. No. 12/109,699, filed Apr. 25, 2008.
U.S. Appl. No. 11/986,489, filed Nov. 21, 2007.
U.S. Appl. No. 12/115,916, filed May 6, 2008.
U.S. Appl. No. 12/045,318, filed Mar. 10, 2008.
U.S. Appl. No. 11/707,831, filed Feb. 16, 2007.
U.S. Appl. No. 12/122,031, filed May 16, 2008.
U.S. Appl. No. 12/170,862, filed Jul. 10, 2008.
U.S. Appl. No. 12/133,109, filed Jun. 4, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/129,784, filed May 30, 2008.
U.S. Appl. No. 12/130,652, filed May 30, 2008.
U.S. Appl. No. 12/163,255, filed Jun. 27, 2008.
U.S. Appl. No. 12/129,880, filed May 30, 2008.
U.S. Appl. No. 12/133,953, filed Jun. 5, 2008.
U.S. Appl. No. 12/169,868, filed Jul. 9, 2008.
U.S. Appl. No. 11/796,035, filed Apr. 26, 2007.
U.S. Appl. No. 11/981,134, filed Oct. 31, 2007.
United States Patent Application entitled Endoscopic Translumenal Articulatable Steerable Overtube, filed Jul. 14, 2008.
United States Patent Application entitled Endoscopic Translumenal Flexible Overtube, filed Jul. 14, 2008.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.

(56) References Cited

OTHER PUBLICATIONS

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DN delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
K. Sumiyama et al., "Endoscopic Caps," Tech. Gastrointest. Endosc., vol. 8, pp. 28-32, 2006.
How StuffWorks "How Smart Structures Will Work," . http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.

\* cited by examiner

TISSUE APPOSITION CLIP APPLICATION DEVICES AND METHODS

FIELD OF THE INVENTION

The present invention relates, in general, to surgical devices and methods of use and, more particularly, to devices and methods for closing a hole or defect in a wall of tissue such as the wall of an organ.

BACKGROUND OF THE INVENTION

Access to the abdominal cavity may, from time to time, be required for diagnostic and therapeutic endeavors for a variety of medical and surgical diseases. Historically, abdominal access has required a formal laparotomy to provide adequate exposure. Such "open" procedures which require incisions to be made in the abdomen are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with a flexible or rigid endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. The trocar must pass through several layers of overlapping tissue/muscle before reaching the abdominal or peritoneal cavity. One of the most significant problems associated with such surgical procedures is the need to provide a secure closure of the peritoneal access site that is required for endoscope passage and, for example, specimen removal. Prior methods required the surgeon to close each of the muscle layers after the procedure is completed.

Still less invasive treatments include those that are performed through insertion of an endoscope through a natural body orifice to a treatment region such as, but not limited to within the peritoneal cavity. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™. Examples of this approach include, but are not limited to, cystoscopy, hysteroscopy, esophagogastroduodenoscopy, and colonoscopy. However, those procedures that involve forming a hole or passage through tissue such as, but not limited to, the stomach, the colon, the vaginal wall, esophagus, etc. still face the challenges associated with securely closing that hole or passage upon completion of the procedure.

Consequently a need exists for devices and methods that can be employed through a patient's natural orifice for closing a passage, hole, defect, incision, etc. made or otherwise ocurring through a wall of tissue such as, for example, the stomach wall, as well as those passages or holes occurring or extending through other tisssues, organs, etc.

The foregoing discussion is intended only to illustrate some of the shortcomings present in the field of the invention at the time, and should not be taken as a disavowal of claim scope.

SUMMARY

In one aspect of the invention, there is provided a clip application device that may include an elongate clip magazine that has an axial clip passage therein for receiving a plurality of tissue apposition clips therein. A pair of grasper lumens may be provided in the elongate clip magazine for accommodating grasper devices therethrough to manipulate tissue adjacent to a distal end of the elongate clip magazine. The device may further include an advancement member for applying an advancement motion to the tissue apposition clips in the axial passage to cause the tissue apposition clips to move out of the axial clip passage in seriatum.

In another general aspect of various embodiments of the present invention, there is provided an adapter for installing a tissue apposition clip that has upper and lower clip arms onto tissue. In various embodiments, the adapter may comprise a body portion that is couplable to a distal end of an endoscope and is configured to releasably retain a tissue apposition clip thereon such that the upper and lower clip arms are retained in an open position to enable tissue to be drawn therebetween and thereafter be released onto the tissue upon application of an advancement force to the tissue apposition clip.

In still another general aspect of various embodiments of the present invention, there is provided a surgical method for closing an opening in a tissue wall. The method may include positioning a tissue apposition clip adjacent a distal end of an endoscope and then positioning the tissue apposition clip adjacent the opening. The method may also include grasping tissue through which the opening extends and drawing a portion of the grasped tissue into a clamping position between upper and lower clip arms of the tissue apposition clip. The method may also include advancing the tissue apposition clip onto the portion of grasped tissue.

Another general aspect of various embodiments of the present invention comprises a surgical method for closing an opening in a portion of an organ wall. The method may include the actions of positioning a tissue apposition clip adjacent a distal end of an endoscope and positioning the tissue apposition clip adjacent the opening. The method may further comprise grasping the portion of the organ wall through which the opening extends and drawing the grasped portion of the organ wall into a clamping position between upper and lower clip arms of the tissue apposition clip. In addition, the method may further comprise advancing the tissue apposition clip onto the grasped portion of the organ wall and applying at least one tissue anchor to the grasped portion or organ wall clamped within the tissue apposition clip.

In another general aspect of various embodiments of the present invention, there is a provided a surgical method for closing an opening in a tissue wall. The method may include positioning a distal end portion of a steerable overtube adjacent a portion of the opening. The method may further include inserting a flexible clip magazine into the steerable overtube, the flexible clip magazine supporting a plurality of tissue apposition clips therein such that the upper and lower clip arms thereof are supported in a spaced open position relative to each other. The flexible clip magazine may have a distal end portion received within said end of the steerable overtube such that the tissue apposition clips supported therein may be selectively discharged out through the distal end of the steerable overtube. The method may also include grasping tissue through which the opening extends and drawing a portion of the grasped tissue into a clamping position between upper and lower clip arms of a distal-most one of the tissue apposition clips supported within the distal end of the clip magazine. The method may also include advancing the distal-most tissue apposition clip onto the portion of grasped tissue.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Figure 1:
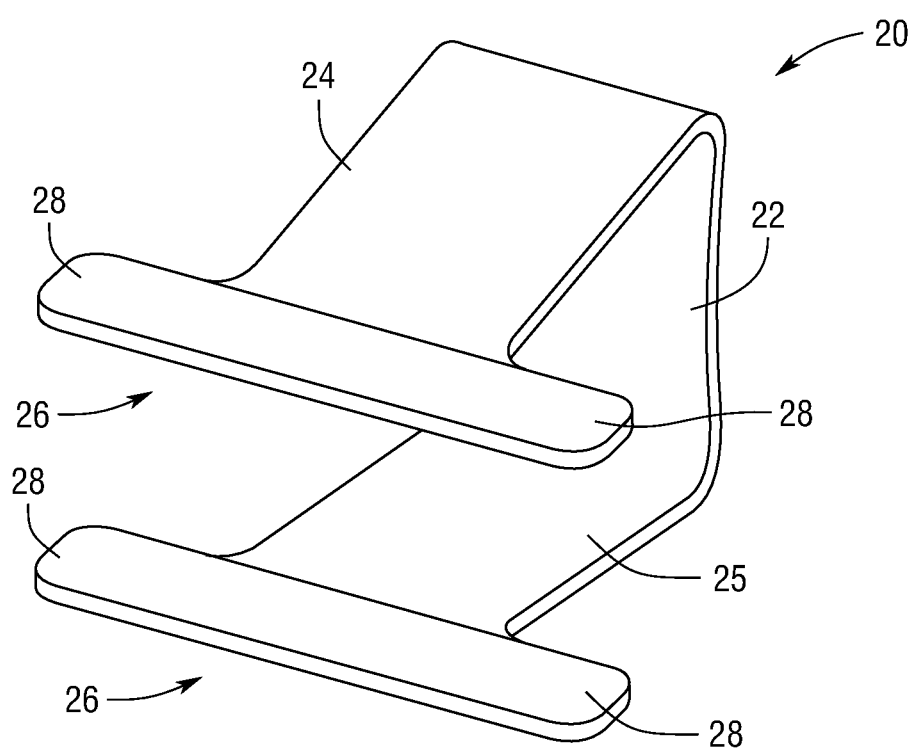
FIG. 1 is a perspective view of a tissue apposition clip embodiment of the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

It will be appreciated that the terms "proximal" and "distal" are used herein with reference to a clinician manipulating an end of the instrument 100 that protrudes out of the natural orifice. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

The present invention generally relates to devices and methods that may be used in connection with the application of tissue apposition clips for closing an opening, hole, passageway, defect, etc. extending through or occurring in a tissue wall. One example of such an opening is known as a "gastrotomy" which comprises an opening formed to gain access to the peritoneal cavity. However, as the present Detailed Description proceeds, it will become readily apparent that the various devices and methods disclosed herein may be successfully employed to apply clips to close various openings, passageways, defects, etc. in a variety of different types of tissue walls, organs, etc. without departing from the spirit and scope of the present invention. "as used herein, the term "tissue wall" is intended to at least encompass all tissues and organs within the human body or animals and includes, but is not limited to, tissue forming the abdominal wall, the stomach, the vaginal walls, the esophagus, the colon, etc. Accordingly, the various devices and methods of the present invention and their respective equivalent structures and methods should not be limited by the nature of the opening to be closed or the particular nature of the tissue through which the openings extend. Furthermore, those of ordinary skill in the art will further appreciate that the devices and methods of the various embodiments of the present invention may also be successfully employed in connection with the application of clips in open or other laparoscopic surgical procedures.

FIG. 1 depicts one embodiment of a tissue apposition clip 20 of the present invention that may be employed to clip a portion of a tissue wall such as, for example, the stomach wall or other tissue as will be discussed in further detail below. In various embodiments, the clips 20 may be fabricated from, for example, stainless steel, Nitinol, titanium or other deformable materials that are implantable within the body and are compatible with that type of environment. As can be seen in FIG. 1, a tissue apposition clip 20 may have a base portion 22 that separates an upper clip arm 24 and a lower clip arm 25 that extend from the base in general confronting relationship to each other. The distal end portions 26 of each clip arm 24, 25 are generally biased towards each other in a "clamping position" or orientation. Each distal end portion 26 may also be formed with two laterally extending protrusions 28, the purpose of which will be discussed below. While the clip 20 depicted in FIG. 1 comprises a preferred tissue apposition clip configuration, other tissue apposition clip configurations could also be employed with the clip application device 100 described below.

In various embodiments, a clip application device 100 of various embodiments of the present invention may be used in connection with a steerable overtube 200. Those of ordinary skill in the art will appreciate that the clip application device 100 may be used in connection with a variety of different steerable overtube arrangements. For example, the steerable overtube 200 may comprise a steerable overtube of the type disclosed in U.S. patent application Ser. No. 11/981,134, filed Oct. 31, 2007, entitled "Endoscopic Overtubes" to Gregory J. Bakos et al., the disclosure of which is herein incorporated by reference in its entirety. Still other overtubes may be employed such as those disclosed in U.S. Pat. No. 5,325,845 to Adair, the disclosure of which is herein incorporated by reference in its entirety. In other embodiments, a steerable overtube of the various types disclosed in commonly owned U.S. patent application Ser. No. 12/172,782, Entitled "Endoscopic Translumenal Articulatable Steerable Overtube" to Gregory J. Bakos et al., filed on even date herewith, now U.S. Pat. No. 8,262,563, and which is hereby incorporated by reference in its entirety, may be successfully employed. In other embodiments, a non-steerable overtube could conceivably be employed, depending upon the application.

Figure 2:
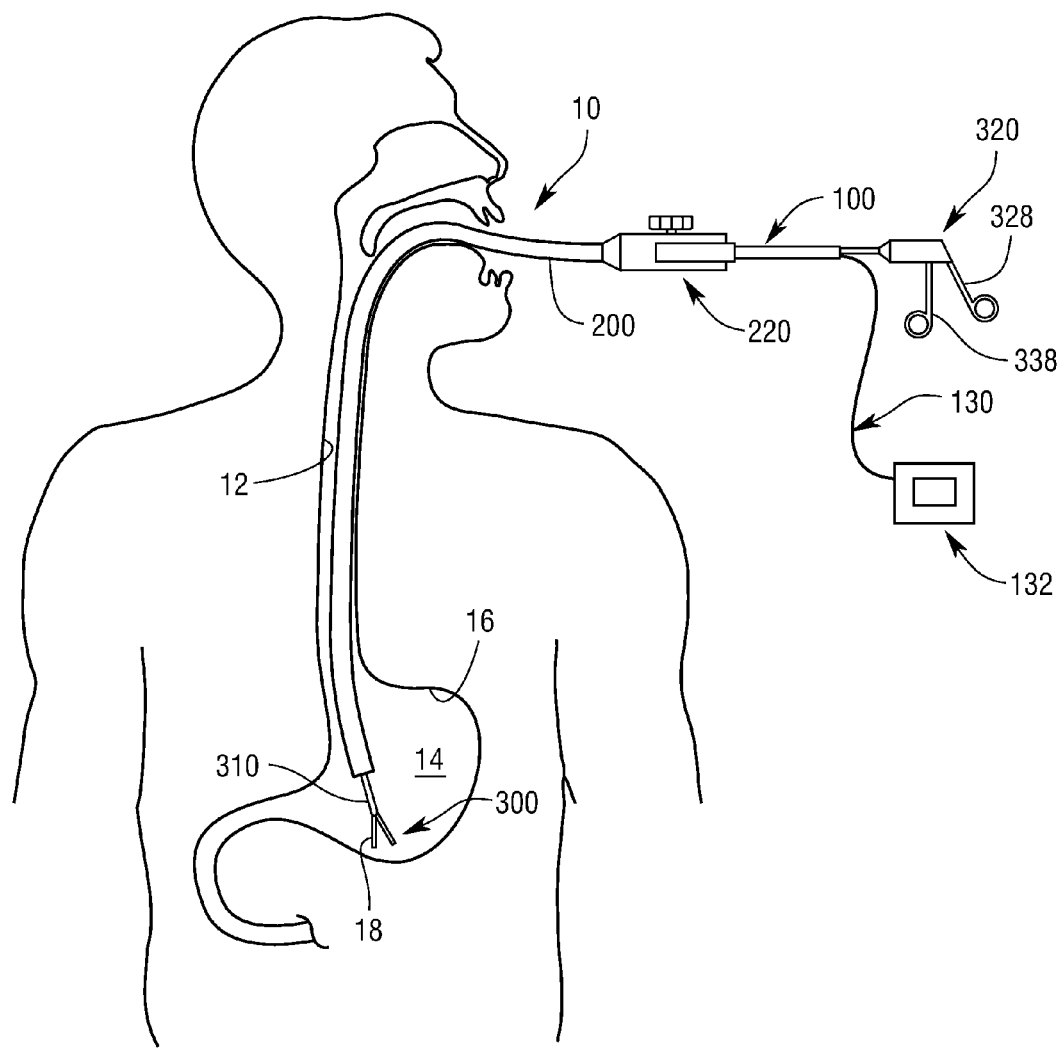
FIG. 2 is diagrammatic view of use of a clip application device embodiment of the present invention inserted through a natural orifice (mouth) of a patient.
Figure 3:
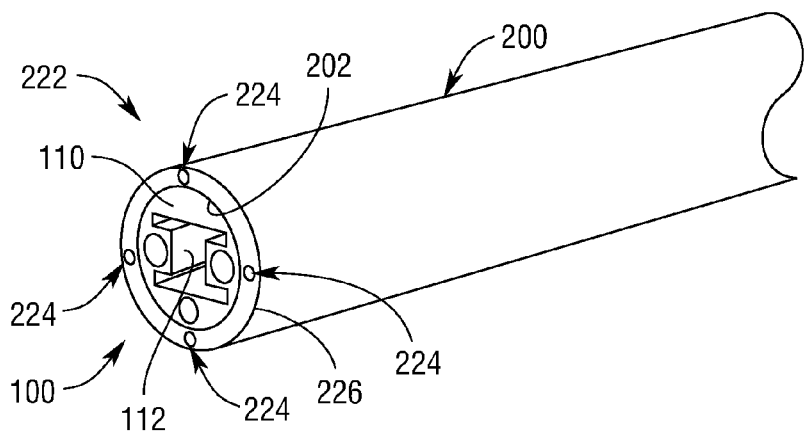
FIG. 3 is a perspective view of portion of a clip application device of the present invention.
Figure 4:
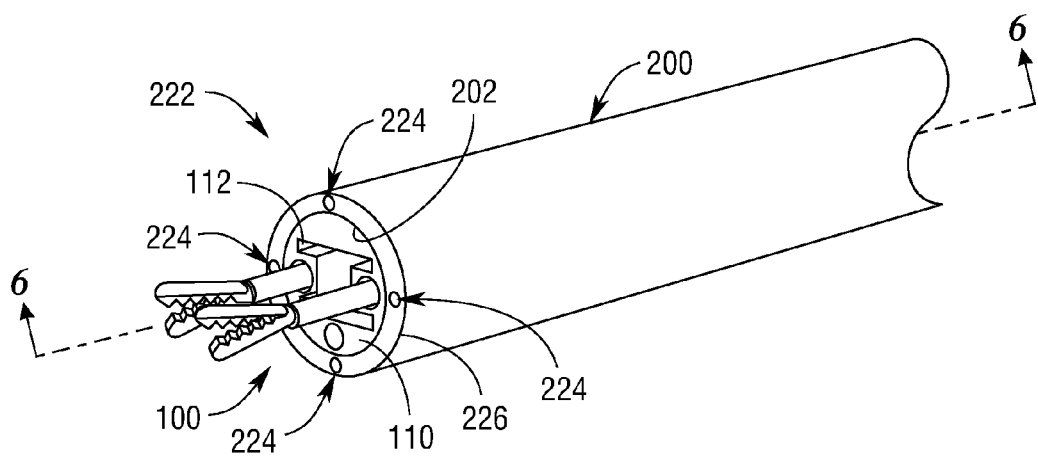
FIG. 4 is another perspective view of a portion of the clip application device of the present invention with graspers extending out of the distal end thereof.

As can be seen in FIG. 2, one version of the steerable overtube 200 may interface with an actuator 220 that is used to articulate the distal end portion 222 of the overtube 200. The steerable overtube 200 has a central lumen 202 through which various endoscopic surgical tool and instruments may pass. See FIGS. 3 and 4. The actuator 220 may be used to selectively apply tension to cables or tension members 224 that extend through the wall 226 of the overtube 200 to draw the distal end portion 222 thereof in a desired direction.

Although, as discussed above, the various embodiments of the present invention may be successfully employed to apply clips to and/or close a hole, passageway, defect, etc. in a variety of different tissue walls and organs, one example in which the clip application 100 has particular utility is the closure of a gastrotomy created through the abdominal wall to gain access to the peritoneal cavity. FIG. 2 illustrates one method of deploying an embodiment of the clip application device 100 of the present invention through a natural orifice to close a gastrotomy. As shown in FIG. 2, the steerable overtube 200 may be inserted through the mouth 10 and esophagus 12 into the stomach 14, for example, to enable the surgeon to create a gastrotomy through a portion of the stomach wall. The gastrotomy may be accomplished utilizing various surgical instruments that are operated through the overtube. Once the gastrotomy has been created and the other surgical procedures have been completed, the surgical tools that have been employed up to this point may be removed from the overtube 200 and a clip application device 100 of the present invention may be inserted through the overtube 200 and into the stomach 14 as shown.

Figure 5:
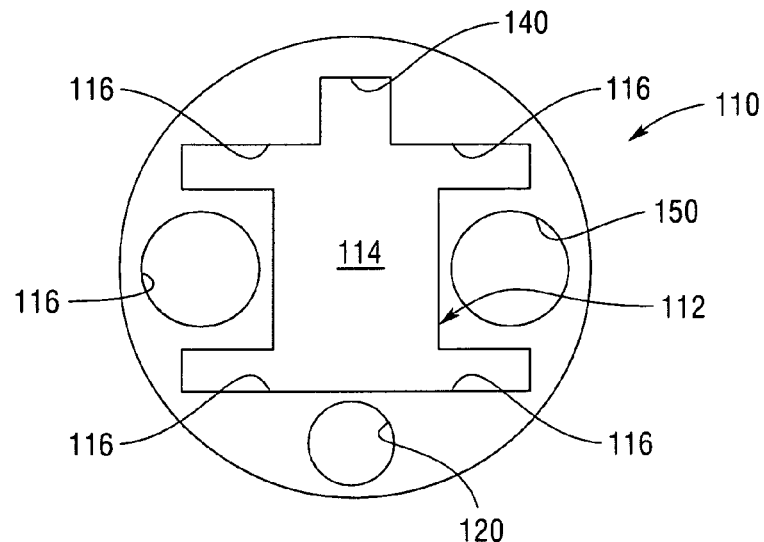
FIG. 5 is an end view of a clip magazine embodiment of the present invention.
Figure 6:
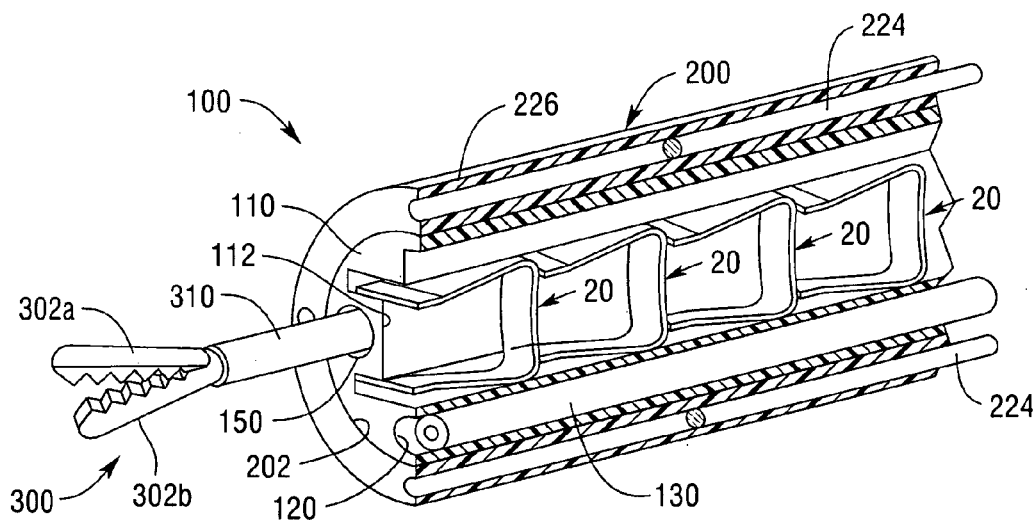
FIG. 6 is a cross-sectional view of the clip application device of FIG. 4 taken along line 6-6 in FIG. 4.

FIGS. 3-6 and 8-10 illustrate one embodiment of the clip application device 100 of the present invention. As can be seen in those Figures, the clip application device 100 may include an elongated clip magazine 110 that is sized to extend through the central lumen 202 in the steerable overtube 200. In various embodiments, the clip magazine 110 may be extruded or otherwise formed from polyurethane, silicone, etc. such that the clip magazine 110 may flex or otherwise conform to the steerable overtube 200. The clip magazine 110 may be formed with a centrally disposed axial clip passage 112 that is shaped to movably accommodate at least one and preferably a series, of clips 20 as illustrated in FIG. 6. As can be seen in FIG. 5, the axial clip passage 112 may have a central passage portion 114 and four leg passage segments 116 that protrude laterally from the central passage portion to accommodate the clip arms of the clips 20. As can be seen in FIG. 6, the leg passage segments 116 may serve to support the upper clip arm 24 and the lower clip arm 25 in a spaced open position relative to each other to enable the clip 20 to be installed over tissue as will be discussed in further detail below.

The clip magazine 110 may further have a channel 120 formed therein for operably supporting a conventional endoscopic video camera 130 that communicates with a video display unit 132 that can be viewed by the surgeon during the operation. See FIG. 2. In addition, an advancement channel 140 may be provided in the clip magazine 110 for accommodating various mechanisms for serially advancing the clips 20 out of the distal end of the clip magazine 110.

Figure 7:
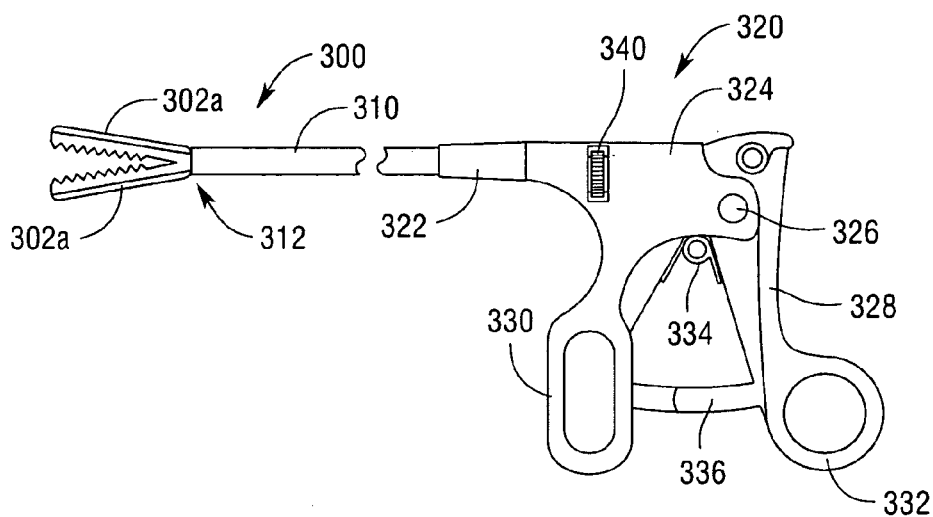
FIG. 7 is a side view of a grasper embodiment.

Also in various embodiments, the clip magazine 110 may be provided with at least one and preferably two lumens 150 for operably accommodating graspers 300. A variety of different known graspers may be employed without departing from the spirit and scope of the present invention. In general, a grasper 300 may include a pair of opposed jaws 302a, 302b that are operably located at a distal end 312 of an elongate shaft 310. The proximal end of elongate shaft 310 may be coupled to a handle assembly 320 at collar 322. The handle assembly 320 may further include a fixed handle 324 that is pivotally engaged at point 326 to a moving handle 328. Handles 324, 328 may have grasping loops 330, 332 attached thereto for the convenient insertion of fingers or a thumb therein. The handle assembly 320 depicted in FIG. 7 includes a spring clip 334 and ratchet 336 as two means of providing bias to handles 330, 332 such that jaws 302a, 302b are urged in a closed position. Though both are pictured here together (for convenience), usually one or the other is used as means to bias jaws shut. The grasper 300 may further have an adjustable knob 340 which causes shaft 310 and therefore jaws 302a, 302b to rotate with respect to fixed handle 330. The jaws 302a, 302b may be opened and closed by manipulating the handles 324, 328. A variety of different graspers and grasper jaw configurations are known and may successfully employed in connection with various embodiments of the present invention. Accordingly, the protections afforded to the various embodiments of the subject invention and their equivalent structures should not be limited to the specific grasper configuration depicted in FIG. 7.

To use the device 100, the graspers 300 are inserted into their respective lumens 150 in the clip magazine 110 such that the jaws 302a, 302b protrude out through the distal end of the clip magazine 110 as shown in FIG. 5. At least one, and preferably a plurality of, clips 20 are inserted in seriatum into the axial clip passage 112 of the clip magazine 110 and may be advanced therein in the distal direction "DD" by an advancement member 350 that may be inserted into the advancement channel 140 in the clip magazine 110. See FIG. 6. While a variety of different clip advancement mechanisms could be used, the clip advancement member 350 may have a distal end 352 that has a notched portion 354 therein for engaging the proximal-most clip 20 to apply a pushing force thereto in the distal direction "DD".

Figure 8:
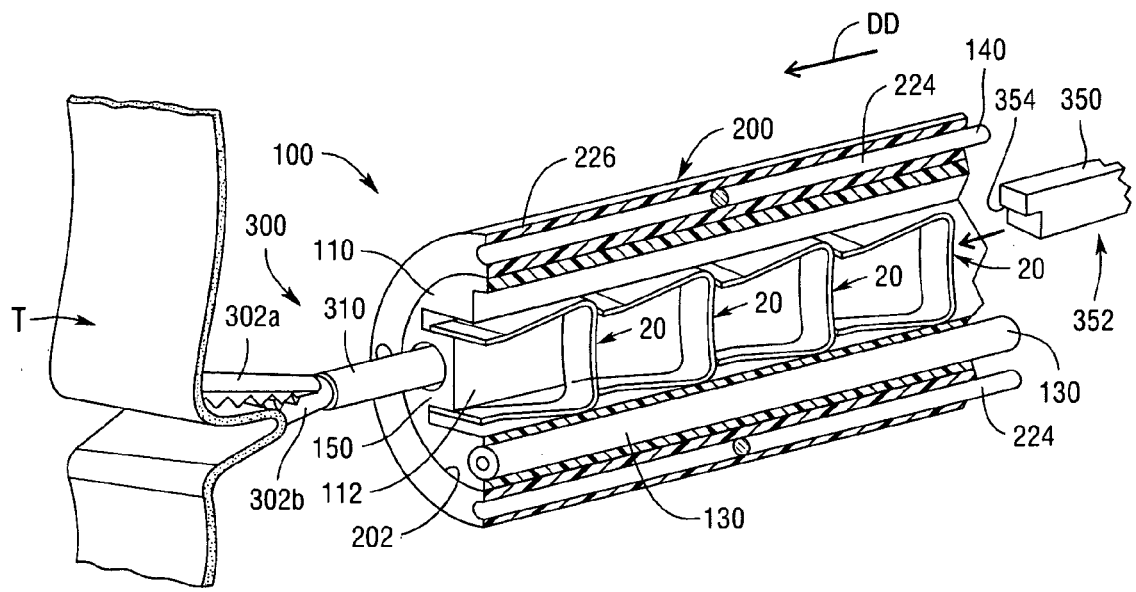
FIG. 8 is another cross-sectional view of the clip application device embodiment of FIG. 6 with one of the graspers thereof gripping tissue.
Figure 9:
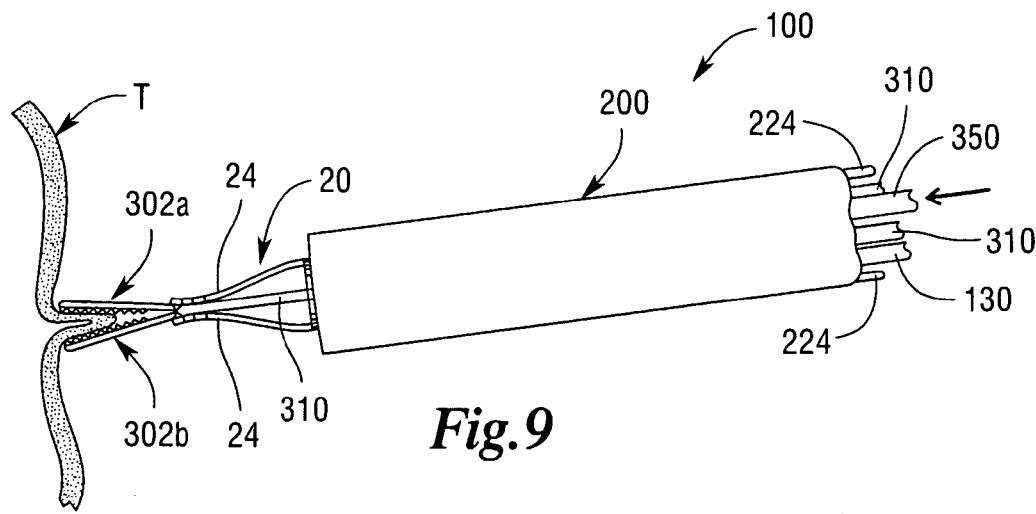
FIG. 9 is a partial side view of the clip application device of FIG. 8.
Figure 10:
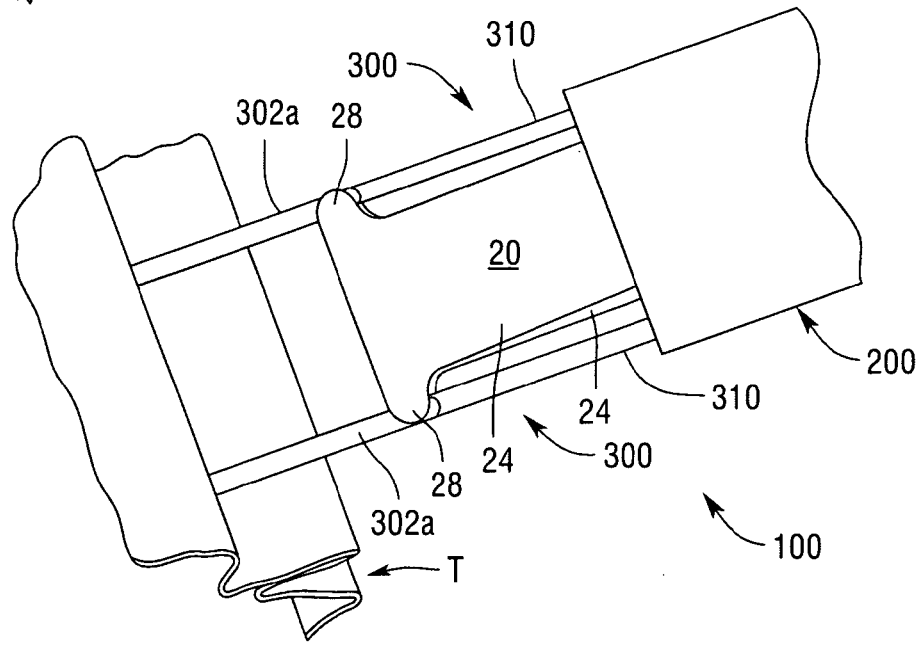
FIG. 10 is a partial perspective view of a portion of the clip applier applying a clip to tissue.
Figure 11:
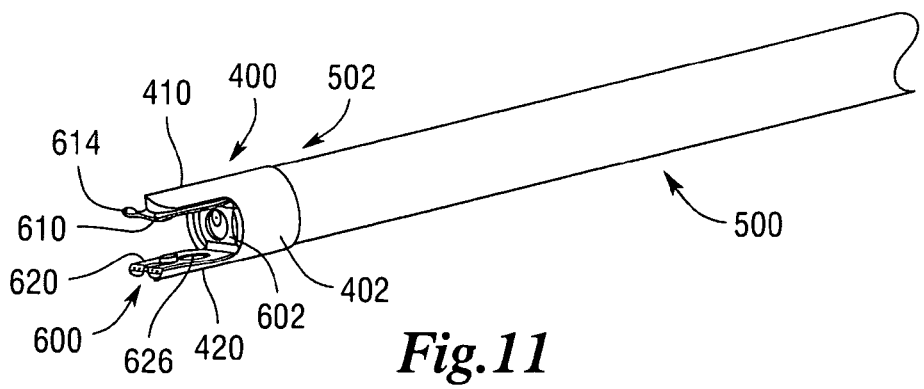
FIG. 11 is a perspective view of another clip application device coupled to an endoscope.

When the surgeon desires to apply the clips 20 to the gastrotomy site, the distal end of the clip application device 100 is inserted in through the patient's mouth 10 or other natural orifice such that the graspers 300 may be extended out of the distal end of the clip magazine 110 to grasp the tissue "T" as shown in FIGS. 8-10. Once the tissue "T" has been acquired by the graspers 300 (as observed by the surgeon by means of the camera 130), the surgeon may then pull the grasped tissue proximally between the spaced upper clip arm 24 and lower clip arm 25 of the distal-most clip 20. The surgeon may also begin to apply an advancement force to the proximal-most clip 20 by inserting the advancement member 350 into the advancement channel 140. The application of such advancement force to the proximal-most clip 20 causes the entire series of clips 20 to move proximally in the clip magazine 110 until the distal-most clip 20 is advanced out of the distal end of the clip magazine 110. As can be seen in FIG. 10, the laterally extending protrusions 28 enable the clip 20 to ride up the elongate shaft 310 and the jaws 302a, 302b of the graspers 300 to retain the upper and lower clip arms 24, 25 in the spaced open position. The clip 20 continues to be advanced until it engages the tissue "T" and disengages the ends of the grasper jaws 302a, 302b. At that point, the clip 20 is holding the tissue folds together and additional clips 20 may be applied in a similar manner or the device 100 may be withdrawn from the patient.

Those of ordinary skill in the art will understand that, although intended to be permanent, these clips 20 may also be designed to slough off intentionally from the clipped tissue to enable the clips to be passed naturally. Although not intended, it is also possible that the clips may come loose from the clipped tissue. In either case, however, it may be desirable for the clips 20 to be sized to enable the clip to pass naturally from the patient without causing harm to the patient. For example, the clips 20 may have smooth rounded edges without significant catch points that could hinder safe passage of the clips 20 from the body.

Figure 12:
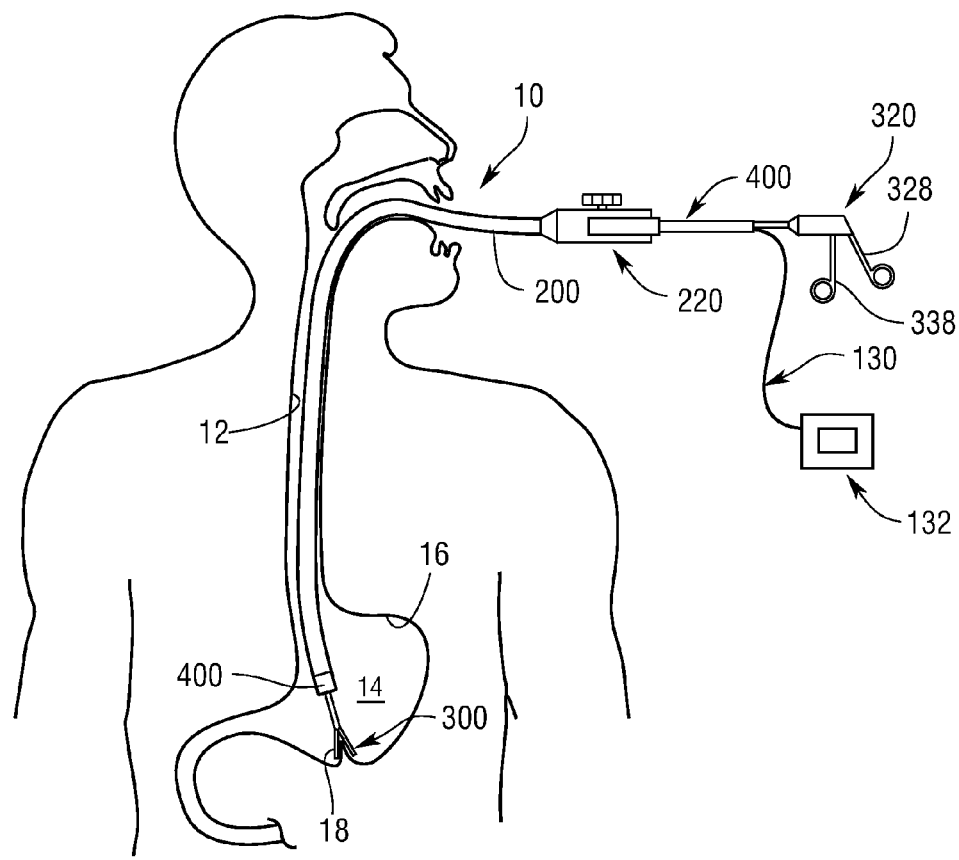
FIG. 12 is a diagrammatic view of use of another clip application device embodiment of the present invention inserted through a natural orifice (mouth) of a patient.
Figure 13:
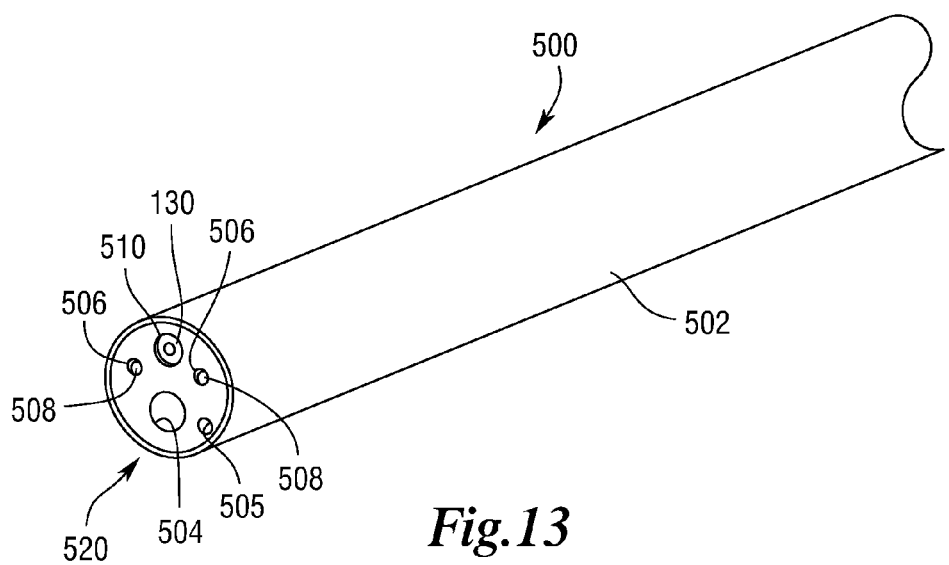
FIG. 13 is a perspective view of an endoscope with which a clip adapter embodiment of the present invention may be used.

FIGS. 11-15 illustrate a clip dispensing adapter 400 that may be used with a conventional endoscope 500. As can be seen in FIG. 12, the endoscope 500 may be passed through the steerable overtube 200 and otherwise guided thereby to the site 18 of the opening in the stomach 14. One form of endoscope 500 that may be employed is illustrated in FIG. 13. As can be seen in that Figure, the endoscope 500 may have an elongate, relatively flexible body 502 that has a working channel or lumen 504 extending therethrough. In addition, the endoscope body 502 may have two or more channels 506 that operably support light bundles 508 therein as well as a camera channel 510 for operably accommodating a video camera 130 therein.

Figure 15:
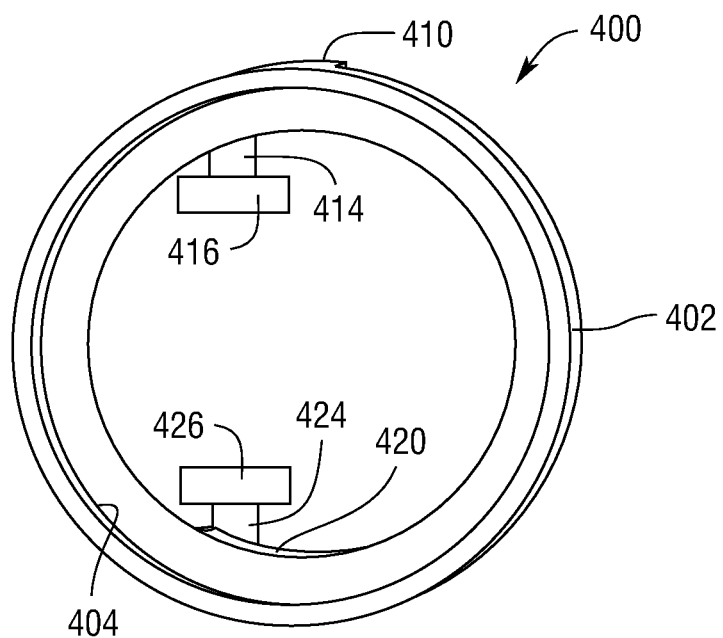
FIG. 15 is an end view of the clip adapter embodiment of the FIG. 14.
Figure 16:
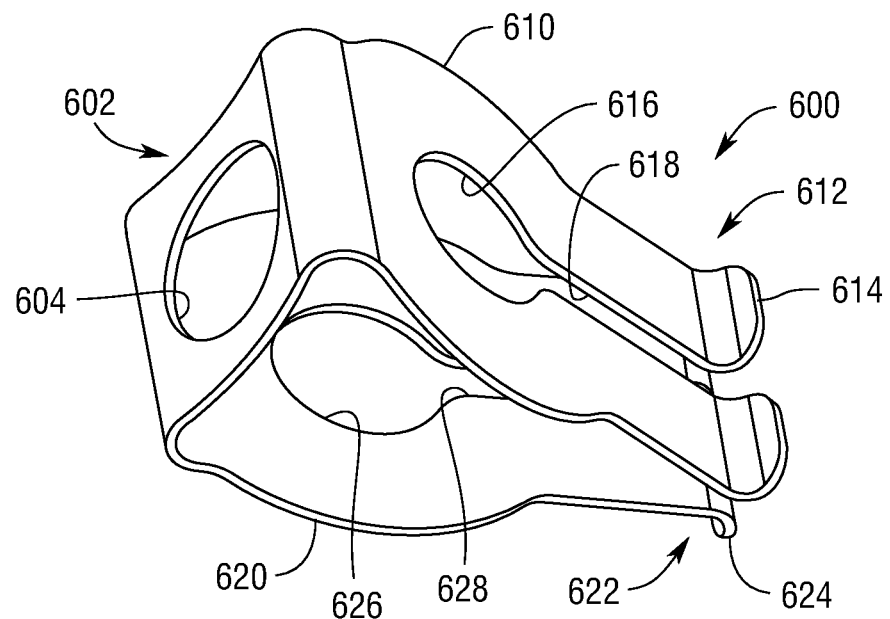
FIG. 16 is a top perspective view of another a tissue apposition clip embodiment of the present invention.

On embodiment of a clip dispensing adapter 400 is depicted in further detail in FIGS. 15 and 16. As can be seen in those Figures, the clip dispensing adapter 400 has a body portion 402 that is sized to fit over the distal end 520 of the endoscope 500. In various embodiments, the body portion 402 has an endoscope-receiving cavity 404 therein that may have an inner diameter that is sized relative to the outer diameter of the distal end 520 of the endoscope 500 such that a frictional fit is established therebetween when the adapter 400 is installed onto the distal end 520. See FIG. 15. For example, in such embodiment, the adapter may be fabricated from, for example, stainless steel, polycarbonate, aluminum, etc. In other embodiments, the adapter 400 may be affixed to the distal end 520 of the endoscope 500 by an appropriate adhesive. In still other embodiments, the adapter 400 may be fabricated from a somewhat elastic material such as, for example, silicone, polyurethane, etc. to enable the adapter 400 to be slid over the distal end 520 of the endoscope 500 and retained thereon. In yet other embodiments, the adapter 400 and the distal end 520 of the endoscope 500 may be configured with threads, bayonet-type connections, ratchet connections, etc. to enable the adapter 400 to be removed from the endoscope 500 if so desired. In other embodiments, the adapter 400 may be permanently affixed or otherwise integrally formed into the distal end 520 of the endoscope 500.

Figure 14:
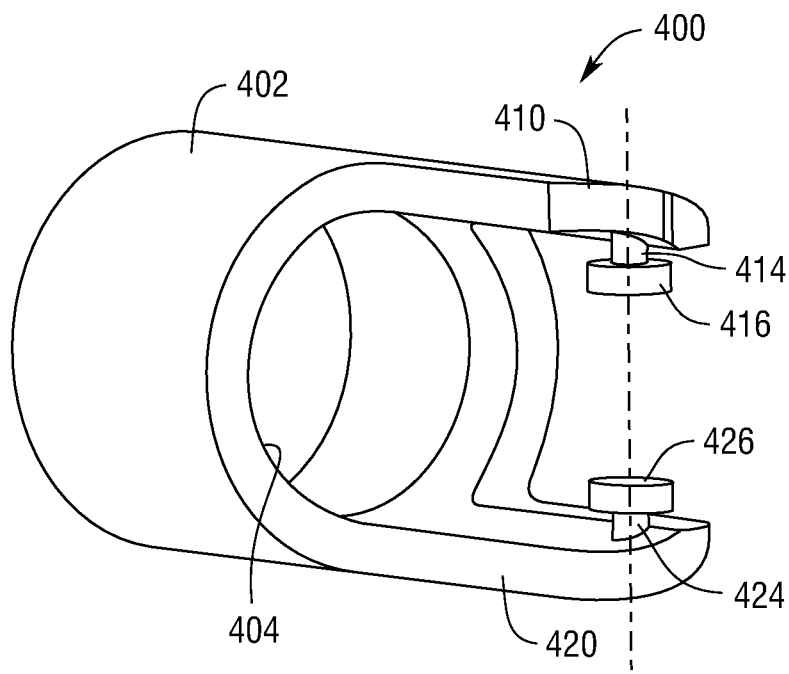
FIG. 14 is a perspective view of a clip adapter embodiment of the present invention.
Figure 17:
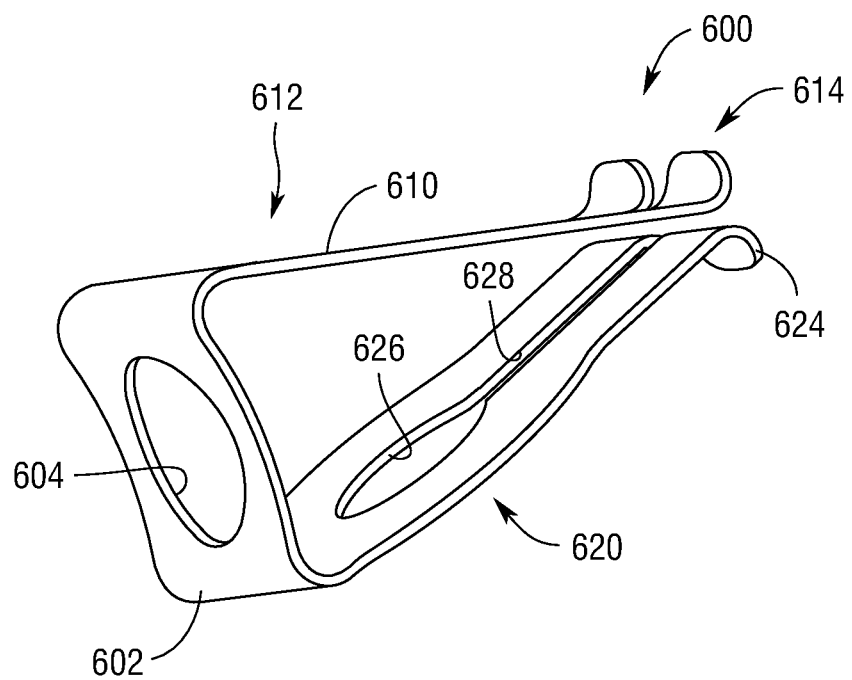
FIG. 17 is a side perspective view of the tissue apposition clip of FIG. 16.

As can be seen in FIGS. 14 and 15, the adapter 400 may further include an upper support arm 410 and a lower support arm 420 that protrude outward from the distal end of the body portion 402. The support arms 410, 420 are spaced from each other to receive a tissue apposition clip 600 therebetween. One example of a tissue apposition clip 600 that may be employed is depicted in FIGS. 16 and 17. In various embodiments, the clip 600 may be fabricated from, for example, stainless steel, Nitinol, titanium, hard plastic, etc. and have a base portion 602 that separates an upper clip arm 610 and a lower clip arm 620 that extend from the base in general confronting relationship to each other. The distal end portion 612 of the upper clip arm 610 and the distal end 622 of the lower clip arm 620 are generally biased towards each other in a "clamping orientation". The distal end 612 may have a folded end portion 614 and the distal end 622 may have a folded end portion 624. The end portions 614 and 624 help to facilitate installation of the clip 600 as it is advanced over folded tissue. In various embodiments, the upper clip arm 610 may have an upper opening 616 therein and an upper slot 618 that extends from the upper opening 616 through the distal end portion 612. Similarly, the lower clip arm 620 has a lower opening 626 and a lower slot 628 extending from the lower opening 626.

Figure 18:
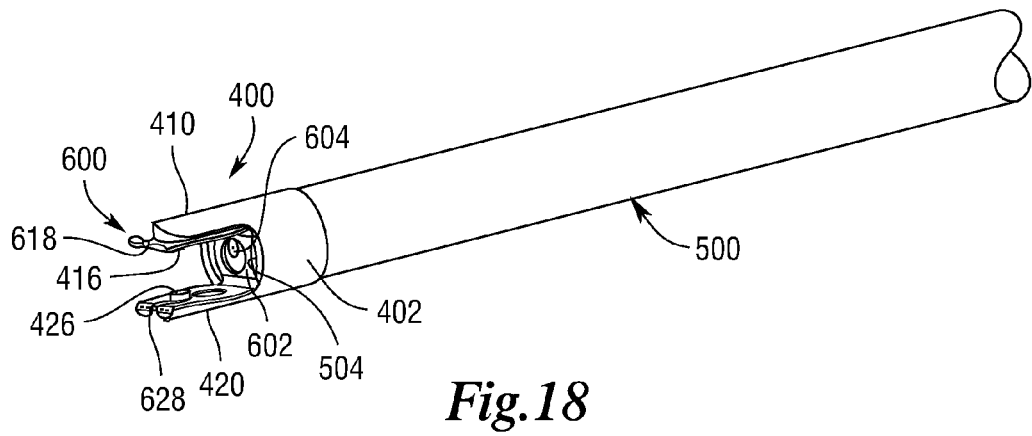
FIG. 18 is a perspective view of a clip dispenser adapter embodiment on an endoscope.
Figure 19:
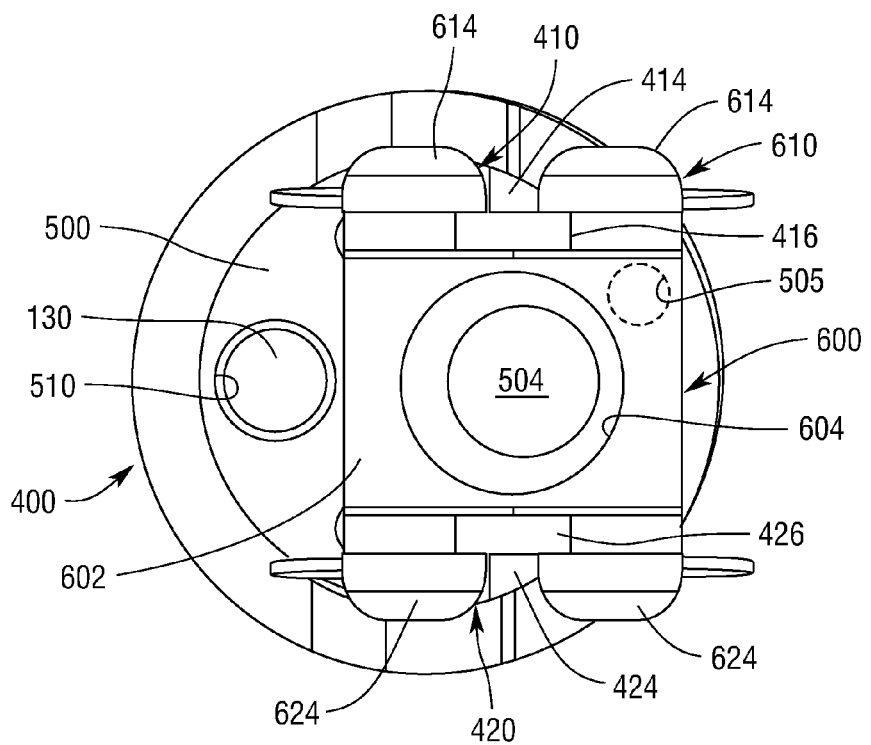
FIG. 19 is an end view of the clip dispenser adapter embodiment and endoscope of FIG. 18 with a tissue apposition clip installed therein.

FIGS. 18-21 illustrate use of the tissue apposition clip 600 with the adapter 400. For example, as can be seen in FIG. 18, the tissue apposition clip 600 may be positioned between the upper support arm 410 and the lower support arm 420. Upper support arm 410 may have a downwardly extending post 414 that has retainer lug 416 formed thereon that is sized to be received in the upper opening 616 in the upper clip arm 610. Similarly, the lower support arm 420 may have an upwardly extending post 424 that has a retainer lug 426 thereon that is sized to be received in the lower opening 626 in the lower clip arm 620. Thus, to install the tissue apposition clip 600 onto the adapter 400, the tissue apposition clip 600 is oriented between the upper support arm 410 and the lower support arm 420 such that the upper retainer lug 414 extends into the opening 616 and the lower retainer lug 424 extends into the opening 626. The tissue apposition clip 600 is then moved distally such that the post 414 is received in the upper slot 618 and the lower post 424 is received in the lower slot 628 of the clip 600 in the "open" position shown in FIG. 18.

Figure 20:
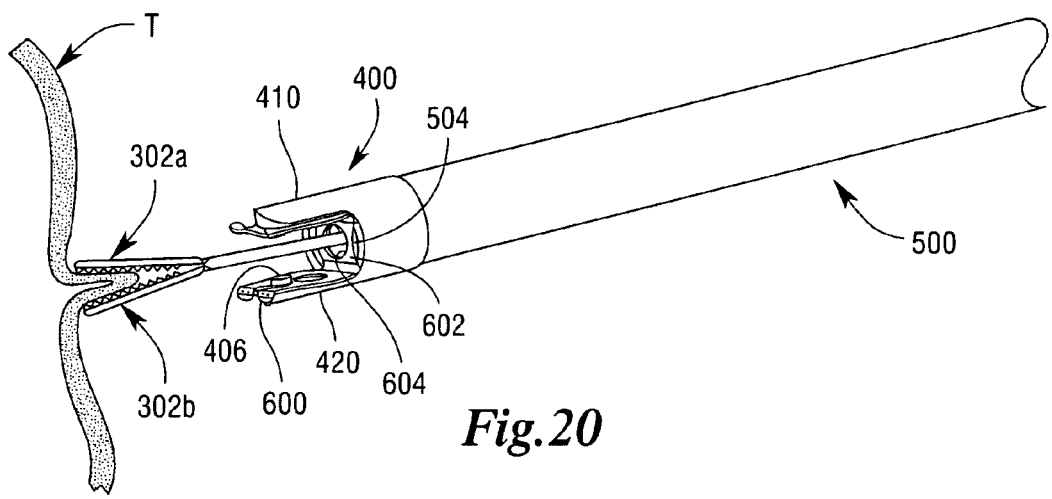
FIG. 20 is a side perspective view of the clip dispenser adapter embodiment of FIG. 19 with a grasper protruding out through the distal end thereof to grasp tissue.
Figure 21:
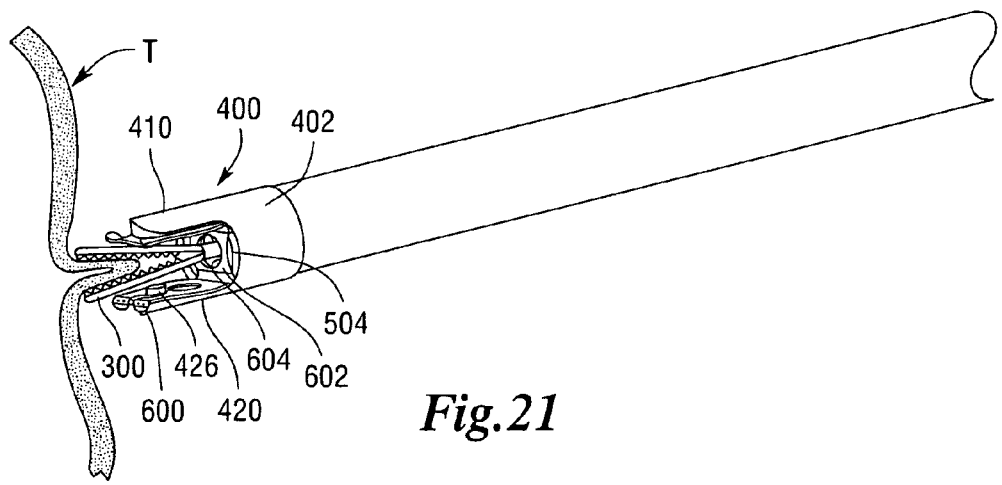
FIG. 21 is another perspective view of the clip dispenser adapter embodiment of FIG. 20 illustrating the grasper pulling tissue in between the clip arms of a clip installed therein.

As can be seen in FIGS. 18-21, the base portion 602 of the clip 600 may have a hole 604 therethrough that is aligned with a working channel 504 in the endoscope 500 when the clip 600 is installed onto the adapter 400. This alignment of hole 604 with the working channel 504 enables a grasper 300 to be inserted therethrough to grasp the tissue "T" as shown in FIGS. 20 and 21. Once the surgeon has grasped the target tissue "T" with the grasper 300 in the manner described above and as illustrated in FIG. 20, the surgeon can then pull the grasper 300 and tissue "T" proximally into the open tissue apposition clip 600 as shown in FIG. 21. While the surgeon is pulling the grasper 300 and tissue "T" proximally, the tissue apposition clip 600 may be pushed onto the tissue by advancing an advancement member (rod, bar, other surgical instrument, etc.) through the working channel 505 to contact the clip base 602 and push it distally onto the tissue "T". When the tissue apposition clip 600 is pushed distally, the lugs 416, 426 will enter the holes 616, 626, respectively in the tissue apposition clip to enable the tissue apposition clip 600 to disengage from the adapter 400 and remain on the tissue "T" as the grasper 300 is withdrawn through the hole 604 and working channel 504.

Figure 22:
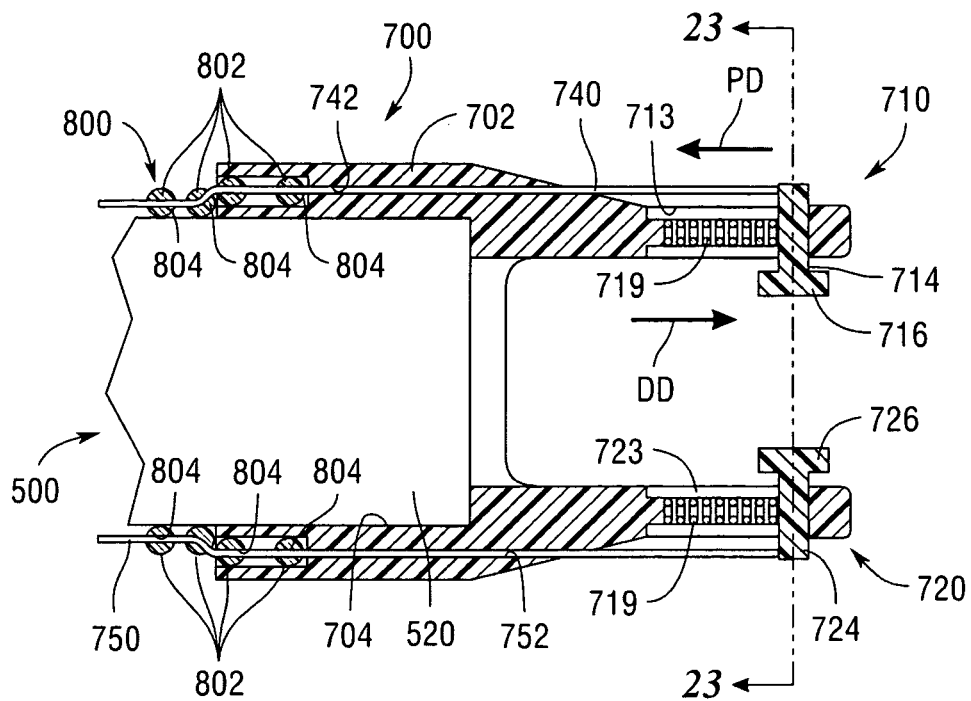
FIG. 22 is a partial cross-sectional view of yet another embodiment of a clip dispenser adapter embodiment of the present invention attached to the distal end of an endoscope.
Figure 23:
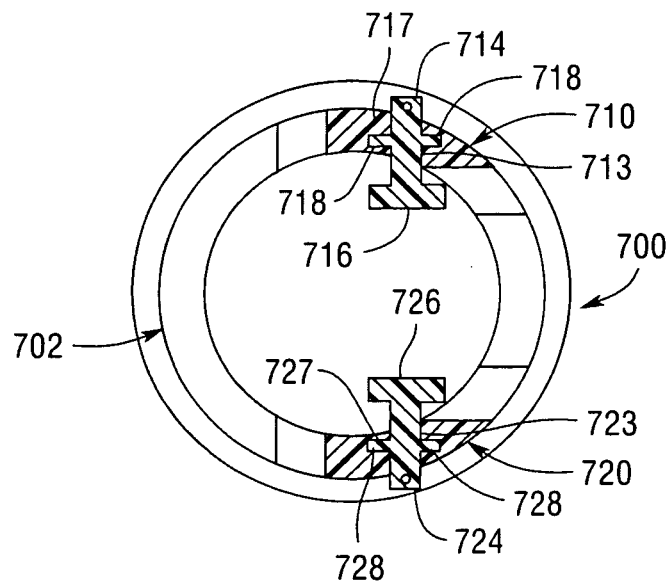
FIG. 23 is a partial cross-sectional end view of the clip dispenser adapter embodiment of FIG. 22.

FIGS. 22 and 23 illustrate another clip dispensing adapter 700 that may be effectively used in connection with the tissue apposition clips 600 described above. As can be seen in those Figures, the clip dispensing adapter 700 has a body portion 702 that is sized to fit over the distal end 520 of the endoscope 500. In various embodiments, the body portion 702 may have an endoscope-receiving cavity 704 therein that may have an inner diameter that is sized relative to the outer diameter of the distal end 520 of the endoscope 500 such that a frictional fit is established therebetween when the adapter 400 is installed onto the distal end 520. For example, in such embodiment, the adapter may be fabricated from stainless steel, aluminum, hard plastic, etc. In other embodiments, the adapter 700 may be affixed to the distal end 520 of the endoscope 500 by an appropriate adhesive. In still other embodiments, the adapter 700 may be fabricated from a somewhat elastic material such as, for example, silicone, polyurethane, elastomer, etc. to enable the adapter 700 to be slid over the distal end 520 of the endoscope 500 and retained thereon. In yet other embodiments, the adapter 700 and the distal end 520 of the endoscope 500 may be configured with threads, bayonet-type connections, ratchet connections, etc. to enable the adapter 700 to be removed from the endoscope 500 if so desired. In other embodiments, the adapter 700 may be permanently affixed or otherwise integrally formed into the distal end 520 of the endoscope 500.

Figure 24:
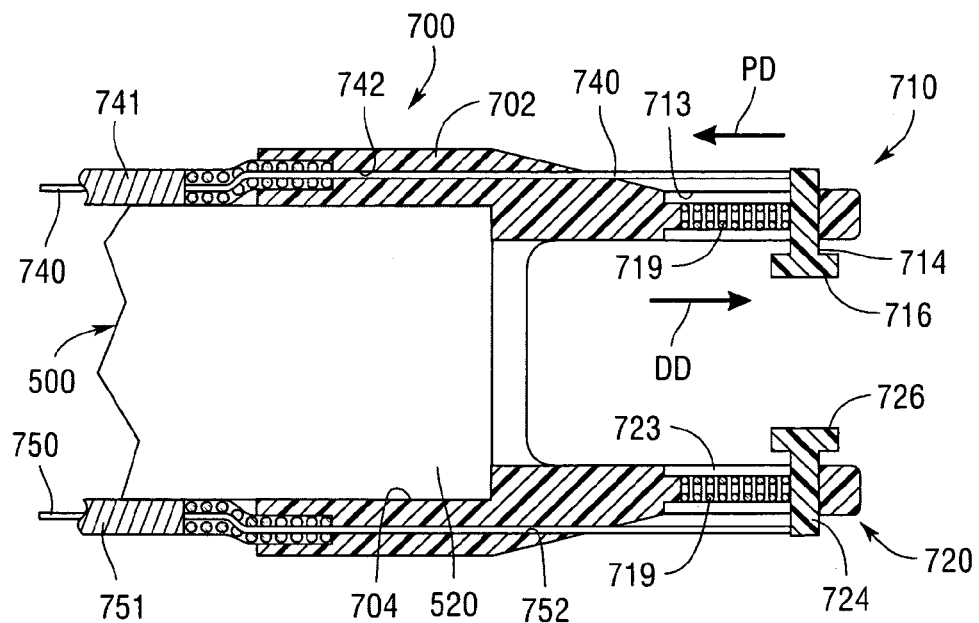
FIG. 24 is a partial cross-sectional view of yet another embodiment of a clip dispenser adapter embodiment of the present invention attached to the distal end of an endoscope.

As can be seen in FIGS. 22 and 23, the adapter 700 may further include an upper support arm 710 and a lower support arm 720 that protrude outward from the distal end of the body portion 702. The support arms 710, 720 are spaced from each other to receive a tissue apposition clip 600 therebetween. Upper support arm 410 has a downwardly extending movable post 714 that has retainer lug 716 formed thereon that is sized to be received in the upper opening 616 in the upper clip arm 610. As can be seen in FIGS. 22 and 23, the movable post 714 is movably supported within a slot 713 in the upper support arm 710. In various embodiments, the movable post 714 may have laterally protruding fins 718 that are received in corresponding slots 717 in the upper support arm 710 such that the movable support post 714 can move in the proximal direction "PD" and the distal direction "DD". The movable support arm 714 is biased into a retention position shown in FIG. 23 by an upper biasing member 719. Similarly, the lower support arm 720 has an upwardly movable post 724 that has a retainer lug 726 thereon that is sized to be received in the lower opening 626 in the lower clip arm 620. As can be seen in FIGS. 23 and 24, the movable post 724 is movably supported within a slot 723 in the lower support arm 720. In various embodiments, the movable post 724 may have laterally protruding fins 728 that are received in corresponding slots 727 in the lower support arm 720 such that the movable support post 724 can move in the proximal direction "PD" and the distal direction "DD". The movable support arm 724 is biased into a retention position shown in FIG. 23 by a lower biasing member 729.

As can also be seen in FIG. 22, an upper retraction cable 740 extends through a passage 742 in the adapter 700 and is affixed to the upper movable support post 714 and a lower retraction cable 750 extends through a passage 752 in the adapter 700 and is affixed to the lower movable support post 724. The upper and lower retraction cables 740, 750 extend through corresponding passages in a flexible tube 800 that extends over the endoscope 500. In various embodiments, the tube 800 may include a helical wound coil of material that can flex with the endoscope 500 and is substantially coextensive therewith. For example, the flexible tube 800 may be fabricated from stainless steel wire. The various coils 802 of the flexible tube may be provided with corresponding holes 804 through which the retraction cables 740, 750 extend. The distal end 810 of the flexible tube 800 may extend into a retention cavity 760 formed in the proximal end of the adapter body 702 and be attached thereto, by pins, screws, adhesive, etc. The flexible tube 800 serves to guide the retraction cables 740, 750 along the endoscope 500 and out through the patient's mouth or other natural orifice. Pulling on the retraction cable 740 in the proximal direction "PD, causes the upper movable post 714 to move in the proximal direction. Likewise, pulling on the retraction cable 750 in the proximal direction "PD" causes the lower movable post 724 to move in the proximal direction. In alternative embodiments, each cable 740, 750 could extend through its own dedicated flexible coil pipe 741, 751, respectively, which would extend alongside of the endoscope. See FIG. 24.

To install the clip 600 onto the adapter 700, the clip 600 is oriented between the upper support arm 710 and the lower support arm 720. Once positioned in the adapter 700, the surgeon may then apply retraction forces to the retraction cables 740, 750 in the proximal direction such that the upper retainer lug 716 extends into the opening 616 and the lower retainer lug 726 extends into the opening 626 in the clip 600. The surgeon may then release the retraction cables 740, 750 and the upper biasing member 719 biases the upper movable post 714 into the retention position and the lower biasing member 729 biases the lower movable post 724 into the retention position to retain the clip 600 in position between the upper and lower support arms 710, 720. The surgeon may then insert a grasper (not shown) through the working channel in the endoscope 500 and through the clip 600 to grasp the tissue in the manner described above and then pull the tissue into a position between the upper and lower clip arms 610, 620. The surgeon may then pull the retraction cables to enable the upper and lower retainer lugs 716, 726 to extend into the respective openings 616 and 626 in the clip 600 to thereby enable the clip to be pushed into the distal direction "DD" by a discharge member, bar, surgical tool inserted through the discharge lumen in the endoscope. Again the surgeon releases the grasper from the tissue and retrieves the grasper from the working channel. The clip 600 remains installed on the tissue and the endoscope may then be withdrawn from the patient to enable another clip 600 to be installed on the adapter if addition clips are required and the process then be repeated again.

Another feature of clip 600 is the ability to facilitate the installation of tissue anchors or sutures to the clipped tissue by passing a tissue anchor applier 900 through the endoscope 500 and through the hole 604 in the clip 600 as shown in FIG.

Figure 25:
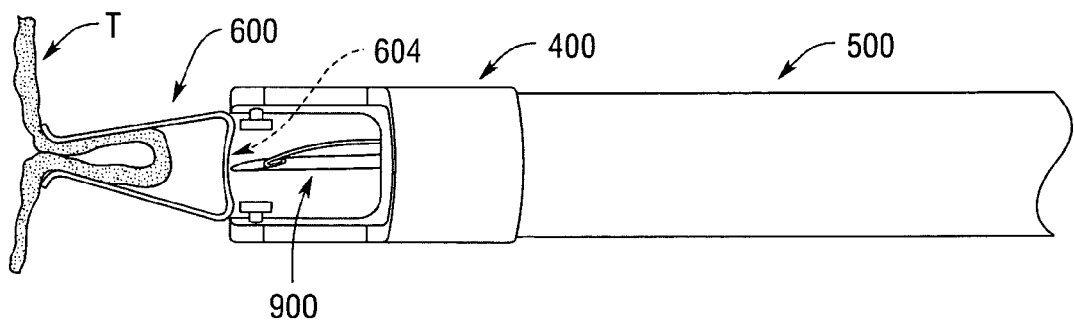
FIG. 25 is a side view of a clip and clip dispenser embodiment of the present invention being employed with a tissue anchor applier.

25. A variety of such tissue anchor appliers are known. For example, tissue anchor applier 900 may comprise any of the tissue anchor applying devices disclosed in any of the following cited documents, the disclosures of which are each herein incorporated by reference in their respective entireties: (i) U.S. Patent Application Publication No. US2008/0103527 A1 to David T. Martin et al., entitled "Flexible Endoscopic Suture Anchor Applier", Ser. No. 11/553,489, filed Oct. 27, 2006. (ii) U.S. Patent Application Publication No. US 2007/0270907 A1, to Michael J. Stokes et al., entitled "Suture Locking Device", Ser. No. 11/437,440, filed May 19, 2006, (iii) U.S. Patent Application Publication No. US 2007/0270889 A1 to Sean P. Conlon et al., entitled "Combination Knotting Element and Suture Anchor Applicator", Ser. No. 11/437,864, filed May 19, 2006, and (iv) pending co-owned U.S. patent application Ser. No. 11/796,035 to David Stefanchik et al., entitled "Surgical Suturing Apparatus", filed Apr. 26, 2007. As can be seen in FIG. 25, the needle portion 902 of the tissue anchor applier 900 is introduced through the endoscope 500 to enable it to pierce through the tissue "T" on both sides of the opening. For example, when the opening comprises a gastrotomy, the needle 902 of the tissue anchor applier 900 may be able to pierce the tissue "T" on both sides of the gastrotomy while remaining in the stomach. This may be a significant safety advantage when compared to use of prior closure systems. For example, when employing prior closure systems and methods, a mucosa-mucosa apposition is created. When employing the clip 600 of the present invention, a serosa-to-serosa apposition is created which may result in a more secure/permanent healing of the gastrotomy.

As can be readily appreciated from the foregoing, the various embodiments of the present invention described above represent a vast improvement over prior devices and methods used to apply tissue apposition clips for closing gastrotomies. The unique and novel features of the various embodiments of the present invention enable the operation to be performed through a natural orifice in the patient and thereby avoid several disadvantages associated with other conventional surgical methods and procedures that require incisions to be made into the abdomen. The present invention may comprise a device that contains several clips that may be serial advanced onto tissue that is grasped and manipulated using conventional tissue grasping devices. Other embodiments may comprise a clip dispensing adapter that may be applied to a distal end of a conventional endoscope and, if desired, supplied and/or sold separately from the endoscope. Such adapters may be pressed onto, threaded onto or otherwise temporarily attached to the distal end of the endoscope to complete the above-described procedure and thereafter removed from the endoscope and discarded or reprocessed for future use. Other embodiments of the present invention contemplate permanent attachment of the adapter to the distal end of the endoscope and still other embodiments envision that the adapter may be integrally formed on the distal end of the endoscope.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the inventions described herein will be processed before surgery. First a new or used endoscope is obtained and, if necessary, cleaned. The endoscope can then be sterilized. In one sterilization technique, the endoscope is placed in a closed and sealed container, such as a plastic or TYVEK® bag. The container and endoscope are then placed in a field of radiation that can penetrate the container, such as gamma radiation, x-rays, or higher energy electrons. The radiation kills bacteria on the endoscope and in the container. The sterilized endoscope can then be stored in the sterile container. The sealed container keeps the endoscope sterile until it is opened in the medical facility.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A clip application device, comprising:
    an elongate clip magazine having an axial clip passage therein for receiving a plurality of tissue apposition clips therein, wherein each of said tissue apposition clips define a hole therethrough;
    at least one grasper lumen in said elongate clip magazine apart from said axial clip passage and configured to movably accommodate a corresponding grasper device therethrough to manipulate tissue relative to a distal end of said elongate clip magazine, wherein each of said grasper lumen passes through said elongate clip magazine and said holes in the tissue apposition clips; and an advancement member for applying an advancement motion to the tissue apposition clips in said axial clip passage to cause the tissue apposition clips to move out of said axial clip passage in seriatum.

2. The clip application device of claim 1 further comprising at least one camera lumen in said elongate clip magazine for receiving a camera therein.

3. The clip application device of claim 1 wherein the tissue apposition clips each have two clip arms and wherein said axial clip passage is configured to orient the tissue apposition clips to advance onto a portion of each of the grasper devices such that the clip arms of each said tissue apposition clip are biased to an open position away from each other as each of the tissue apposition clips is advanced out of said axial clip passage.

4. The clip application device of claim 1 further comprising an overtube for receiving said elongate clip magazine therein.

5. The clip application device of claim 4 wherein said overtube has a steerable distal end portion.

6. An adapter for installing a tissue apposition clip having upper and lower clip arms onto tissue, said adapter comprising:
a body portion couplable to a distal end of an endoscope having a longitudinal axis;
an upper support arm protruding from said body portion along said longitudinal axis;
a lower support arm protruding from said body portion along said longitudinal axis and having a fixed spacing from said upper support arm to enable a tissue apposition clip to be supported therebetween, wherein said upper and lower support arms are stationary;
an upper retention lug on said upper support arm configured to releasably engage the upper clip arm of the tissue apposition clip;
a lower retention lug on said lower support arm configured to releasably engage the lower clip arm of the tissue apposition clip, said upper and lower retention lugs configured to releasably retain the tissue apposition clip in an open position to enable tissue to be drawn therebetween and thereafter enable the tissue apposition clip to be released therefrom onto the tissue upon application of an advancement force to the tissue apposition clip, wherein said upper and lower retention lugs are selectively movable from a retention position to a releasing position upon application of a release force thereto; and
a tension member corresponding to each said upper and lower retention lug, each said tension member extending through a corresponding flexible tube coextensive with said endoscope.

7. The adapter of claim 6 wherein said body portion is attached to the distal end of the endoscope by a fastener arrangement selected from a group of fastener arrangements consisting of: threads, slide-on type connections, and ratchet connections.

8. The adapter of claim 6 further having an opening through said body portion through which surgical tools may pass.

9. A surgical kit comprising:
a tissue grasping device; and
an adapter of claim 6.

10. A clip application device, comprising:
an elongate clip magazine having an axial clip passage therein, wherein said axial clip passage comprises:
a central passage portion; and
four leg passage segments, wherein two leg passage segments are located at an upper end of said central passage portion and two leg passage segments are located at a lower end of said central passage portion, wherein said leg passage segments protrude laterally from said central passage portion;
wherein said axial clip passage is configured to receive a plurality of tissue apposition clips comprising a base portion, an upper clip arm, a lower clip arm, and two laterally extending protrusions, wherein said leg passage segments are configured to slidably receive said laterally extending protrusions and said central passage portion is configured to slidably receive said base portion;
at least one grasper lumen in said elongate clip magazine apart from said axial clip passage and configured to movably accommodate a corresponding grasper device therethrough to manipulate tissue relative to a distal end of said elongate clip magazine; and
an advancement member for applying an advancement motion to said tissue apposition clips in said axial clip passage to cause said tissue apposition clips to move out of said axial clip passage in seriatum.

11. The clip application device of claim 10 further comprising at least one camera lumen in said elongate clip magazine for receiving a camera therein.

12. The clip application device of claim 10 wherein the tissue apposition clips each have two clip arms and wherein said axial clip passage is configured to orient the tissue apposition clips to advance onto a portion of each of the grasper devices such that the clip arms of each said tissue apposition clip are biased to an open position away from each other as each of the tissue apposition clips is advanced out of said axial clip passage.

13. The clip application device of claim 10 further comprising an overtube for receiving said elongate clip magazine therein.

14. The clip application device of claim 13 wherein said overtube has a steerable distal end portion.

* * * * *